US012779168B2

(12) United States Patent
Prasad et al.

(10) Patent No.: US 12,779,168 B2
(45) Date of Patent: Nov. 3, 2026

(54) MEDICAL DEVICE KIT WITH INTEGRATED ORGANIZATION AND WASTE DISPOSAL FEATURES

(71) Applicant: Becton, Dickinson and Company, Franklin Lakes, NJ (US)

(72) Inventors: Shishir Prasad, Ramsey, NJ (US); Rahul Malviya, Salmon Arm (CA); Sudarsen Varma, Pune (IN); Atharva Shetye, Bangalore (IN); Aishwarya Landekar, Kothrud (IN); Vivek K T, Bengaluru (IN)

(73) Assignee: BECTON, DICKINSON AND COMPANY, Franklin Lakes, NJ (US)

( * ) Notice: Subject to any disclaimer, the term of this patent is extended or adjusted under 35 U.S.C. 154(b) by 83 days.

(21) Appl. No.: 17/979,457

(22) Filed: Nov. 2, 2022

(65) Prior Publication Data

US 2024/0139466 A1 May 2, 2024

(51) Int. Cl.

| | |
|---|---|
| ***A61B 50/36*** | (2016.01) |
| ***A61M 25/00*** | (2006.01) |
| ***B65D 77/00*** | (2006.01) |

(52) U.S. Cl.

CPC ......... *A61M 25/002* (2013.01); *B65D 77/006* (2013.01); *B65D 2203/02* (2013.01); *B65D 2313/02* (2013.01)

(58) Field of Classification Search

CPC ...... A45C 2007/0009; A61B 2050/318; A61B 2050/30; A61B 2050/3008;

(Continued)

(56) References Cited

U.S. PATENT DOCUMENTS 1,885,736 A * 11/1932 Enfant ..................... A45C 1/02 D3/253
1,914,889 A * 6/1933 Lugara ..................... A62B 1/06 224/159

(Continued)

FOREIGN PATENT DOCUMENTS

CN 110510244 A * 11/2019 ............. B65D 31/12
EP 0220038 A2 * 4/1987

(Continued)

OTHER PUBLICATIONS

Extended European Search Report for EP 23886814.5—Date: Sep. 4, 2026 (9 pages).

*Primary Examiner* — Allan D Stevens
(74) *Attorney, Agent, or Firm* — Myers Bigel, P.A.

(57) ABSTRACT

Provided herein is a medical device kit that includes a base sheet having an inner surface and an outer surface and a first base portion and a second base portion, the base sheet configurable between a folded state and an unfolded state. A first waste bin is secured to the first base portion on the inner surface and a second waste bin is secured to the second base portion on the inner surface. A plurality of pockets configured to retain medical supplies therein is attached to the first waste bin, the second waste, or both the first and second waste bins, on an outward facing surface thereof. A plurality of fastening devices is provided configured to secure the first base portion to the second base portion when the base sheet is in the folded state and to selectively seal shut the first waste bin and the second waste bin.

18 Claims, 11 Drawing Sheets

(58) Field of Classification Search

CPC . A61B 2050/314; A61B 50/36; A61B 50/316; A61B 50/37; A61B 2050/316; A61B 2050/375; B65D 31/12; B65D 33/008

USPC ..... 383/37, 38; 224/602, 609; 206/570, 571, 206/572, 438, 440, 441, 466

See application file for complete search history.

(56) References Cited

U.S. PATENT DOCUMENTS

| | | | | | |
|---|---|---|---|---|---|
| 1,995,518 | A * | 3/1935 | Perry | B42F 19/00 | 150/147 |
| 2,672,263 | A * | 3/1954 | Alber | A45F 5/00 | 224/602 |
| 2,674,288 | A * | 4/1954 | Laidlaw | A45C 3/02 | 190/115 |
| 2,813,602 | A * | 11/1957 | Macarthur, Jr. | B62J 9/20 | 383/7 |
| 2,843,170 | A * | 7/1958 | Frankfurt | A45C 11/24 | 150/112 |
| 2,979,098 | A * | 4/1961 | Greaves | B60R 7/043 | 297/188.06 |
| 3,223,233 | A * | 12/1965 | Becker | B65D 77/062 | 206/466 |
| 3,411,264 | A * | 11/1968 | Farquhar | B65D 33/02 | 53/558 |
| 4,086,945 | A * | 5/1978 | Carter | A45C 11/00 | D6/633 |
| 4,391,396 | A * | 7/1983 | Brady | A45F 5/00 | 383/7 |
| 4,796,790 | A * | 1/1989 | Hamilton | A45F 5/021 | 224/675 |
| 4,993,844 | A * | 2/1991 | Robinson | B65D 33/2566 | 383/38 |
| 5,100,000 | A * | 3/1992 | Huseman | B65D 33/2508 | 383/65 |
| 5,419,437 | A * | 5/1995 | Huseman | B65B 43/26 | 383/65 |
| 5,791,476 | A * | 8/1998 | Stekloff | B01L 9/06 | 206/521 |
| 5,971,155 | A * | 10/1999 | Liang | B65D 33/2508 | 383/65 |
| 6,053,634 | A * | 4/2000 | Kay | A45C 9/00 | 383/14 |
| 6,341,894 | B1 * | 1/2002 | Quinones | B65D 33/14 | 383/22 |
| 6,880,971 | B1 * | 4/2005 | Huseman | A47F 13/085 | 383/102 |
| 7,761,944 | B2 * | 7/2010 | Skophammer | A47D 5/006 | 5/655 |
| D658,361 | S | 5/2012 | Kontos | | |
| 8,371,448 | B1 | 2/2013 | Reaux | | |
| 8,707,961 | B1 * | 4/2014 | Kazravan | A61B 50/10 | 128/849 |
| 2002/0014433 | A1 * | 2/2002 | Schneider | B65D 31/12 | 383/93 |
| 2002/0015540 | A1 * | 2/2002 | Price | B65D 33/2541 | 383/38 |
| 2002/0018601 | A1 * | 2/2002 | Nelson | B65D 33/14 | 383/7 |
| 2003/0021500 | A1 * | 1/2003 | Price | B65D 33/2541 | 383/38 |
| 2003/0068101 | A1 * | 4/2003 | Huseman | B65D 33/20 | 383/93 |
| 2004/0222275 | A1 * | 11/2004 | Mt.Pleasant | B42F 7/025 | 229/74 |
| 2005/0053312 | A1 * | 3/2005 | Hankins | A45C 3/00 | 383/4 |
| 2008/0283534 | A1 | 11/2008 | Paz | | |
| 2009/0142006 | A1 * | 6/2009 | Wine | B65D 31/12 | 383/42 |
| 2010/0142861 | A1 * | 6/2010 | Sam | B65D 31/12 | 383/105 |
| 2010/0142862 | A1 * | 6/2010 | Sam | B65D 33/008 | 383/38 |
| 2013/0236128 | A1 * | 9/2013 | Bray | B65D 31/02 | 383/69 |
| 2016/0045381 | A1 | 2/2016 | Spence | | |
| 2016/0263308 | A1 * | 9/2016 | Ngo | A61B 50/30 | |
| 2016/0376084 | A1 * | 12/2016 | Wein | B65D 33/004 | 206/541 |
| 2017/0095048 | A1 | 4/2017 | Kohn et al. | | |
| 2017/0340403 | A1 | 11/2017 | Roberts-Monteleone | | |
| 2018/0235338 | A1 * | 8/2018 | Lamb | A45C 11/182 | |
| 2019/0021463 | A1 | 1/2019 | Oja et al. | | |
| 2020/0383743 | A1 * | 12/2020 | Howell | A61B 46/00 | |
| 2020/0383744 | A1 * | 12/2020 | Mithani | A61B 46/20 | |
| 2022/0297893 | A1 * | 9/2022 | Patel | B65D 31/12 | |

FOREIGN PATENT DOCUMENTS

| | | | | |
|---|---|---|---|---|
| EP | 4450419 | A1 * | 10/2024 | A24F 23/04 |
| FR | 471089 | A * | 10/1914 | |
| FR | 2659531 | A1 * | 9/1991 | |
| GB | 2315479 | A * | 2/1998 | A45C 3/04 |

* cited by examiner

CATHETER REMOVAL KIT – CVC

FLUSHING KIT – PIVC

MEDICAL DEVICE KIT WITH INTEGRATED ORGANIZATION AND WASTE DISPOSAL FEATURES

BACKGROUND OF THE INVENTION

Field of the Invention

The present disclosure relates generally to kits for use in placing, maintaining, altering, and/or removing medical devices in, on, and/or from the body of a patient.

Description of Related Art

Medical device kits (or "convenience kits") are used by medical care providers and clinicians for various medical treatments or surgical procedures. A medical device kit packages together all the medical devices and products that are necessary for the particular treatment or procedure that is to be performed. As one example, catheter kits are available in the market for catheter dressing, catheter flushing, catheter insertion, and catheter removal. Catheter kits, depending on the exact use or application thereof, may include at least some of sterile gloves, alcohol wipes, syringes, gauze, sutures, tape, dressings, disinfecting caps, swab sticks, tourniquets, securement devices, hemostatic agents, and/or anticoagulants, as examples.

Existing medical device kits, including catheter kits as described above, typically have no provision for the efficient organization of the medical supplies included therein. That is, the kit may be in the form of a simple receptacle into which all supplies to be used for a procedure are packaged together, such that the supplies may shift around and mix together, with there being no organization or separation of the supplies. As many medical treatments or procedures may be performed as a step-by-step process, with devices and products in the kit being used in a particular order, it would be desirable for all the supplies in the medical device kit to be organized according to their order of use, so as to improve efficiency of the procedure being performed and minimize the potential for steps in the procedure to be skipped.

In using medical device kits, it is also recognized that proper disposable of the used supplies (i.e., medical waste) from the kit is desirable. As one example, the presence and spillage of medical waste in the work area in which the procedure/treatment is being performed can lead to an intermingling of the medical waste and the supplies in the kit that are still to be used in the procedure/treatment, and this can lead to an increase in time needed to complete the procedure or potentially create unsanitary conditions that can lead to potential infections or other health hazards. It would therefore be desirable for the medical device kit to assist with proper disposal of the medical waste created thereby, so as improve efficiency in performing the procedure/treatment and prevent issues associated with improper disposal of medical waste, including bio-hazard medical waste.

Accordingly, a need exists in the art for medical device kits that address issues of organization and waste disposal as described above.

SUMMARY OF THE INVENTION

Provided herein is a medical device kit for packaging medical supplies for use in a medical procedure. The medical device kit includes a base sheet having an inner surface and an outer surface and a first base portion and a second base portion, the base sheet configurable between a folded state and an unfolded state. The medical device kit also includes a first waste bin secured to the first base portion on the inner surface, a second waste bin secured to the second base portion on the inner surface, and a plurality of pockets configured to retain medical supplies therein, the plurality of pockets attached to the first waste bin, the second waste, or both the first and second waste bins, on an outward facing surface thereof. The medical device kit further includes a plurality of fastening devices configured to secure the first base portion to the second base portion when the base sheet is in the folded state and to selectively seal shut the first waste bin and the second waste bin.

In some embodiments, each of the base sheet and the first and second waste bins is formed of a waterproof, nonwoven fabric.

In some embodiments, each of the first waste bin and the second waste bin is stitched to the base sheet along a bottom edge and side edges of the respective first waste bin or second waste bin, so as to define an opening between the base sheet and the respective one of the first waste bin and the second waste bin.

In some embodiments, the opening of the first waste bin faces a first end of the base sheet and the opening of the second waste bin faces a second end of the base sheet In some embodiments, the plurality of fastening devices is a plurality of hook-and-loop fasteners, with the plurality of hook-and-loop fasteners including a first hook-and-loop fastener positioned to secure the first base portion to the second base portion when the base sheet is in the folded state and additional hook-and-loop fasteners positioned adjacent the openings of the first and second waste bins, to selectively seal the openings.

In some embodiments, the additional hook-and-loop fasteners include a first hook-and-loop fastener strip positioned on an inward facing surface of each of the first and second waste bins, adjacent the opening, and a second hook-and-loop fastener strip positioned on the inner surface of the base sheet, adjacent the opening of each of the first and second waste bins, with the first hook-and-loop fastener strip aligned with the second hook-and-loop fastener strip, such that the first and second hook-and-loop fastener strips are securable together to seal the opening of the respective first waste bin or second waste bin.

In some embodiments, the first base portion and the second base portion are positioned on opposing ends of the base sheet along a lengthwise direction.

In some embodiments, the base sheet includes a tear line formed along a centerline of the base sheet, between the first base portion and the second base portion, the first base portion separable from the second base portion along the tear line.

In some embodiments, the medical device kit is in a storage configuration when the base sheet is in the folded state, with one of the plurality of fastening devices securing the first base portion to the second base portion, and the medical device kit is in a usage configuration when the base sheet is in the unfolded state, with a prep area being provided by a portion of the base sheet between the first waste bin and the second waste bin.

In some embodiments, each of the plurality of pockets is adhered to a respective one of the first waste bin and the second waste bin, so as to be selectively removable therefrom.

In some embodiments, the first waste bin and the second waste bin are labeled or color coded, to differentiate one of the first and second waste bins for receiving packaging waste from the other of the first and second waste bins for receiving hazardous medical waste.

Also provided herein is a medical device kit for packaging medical supplies for use in a medical procedure. The medical device kit includes an outer casing having a left casing region, a center casing region, and a right casing region, the outer casing foldable in the center casing region to fold the left casing region over the right casing region. The medical device kit also includes a plurality of kit pages secured to the outer casing in the center casing region, such that the plurality of kit pages is contained within the outer casing when the left casing region is folded over the right casing region. Each of the plurality of kit pages further includes a right page region having one or more pockets provided thereon each configured to store a medical supply therein and a left page region having instructions thereon regarding use of the medical supply or supplies stored in the one or more pockets on the right page region.

In some embodiments, the plurality of kit pages are arranged sequentially according to an order of use of the medical supplies included in the medical device kit, for an associated medical treatment or procedure for which the medical device kit is used.

In some embodiments, each of the plurality of kit pages comprises one or more color coded tags, the one or more color coded tags indicating a type of waste remaining after usage of the medical supplies on the respective kit page In some embodiments, each of the plurality of kit pages is configured to be torn out from the outer casing, so as to be disposed thereof.

In some embodiments, used medical supplies are returned into their respective pocket and are disposed of when the respective kit page is torn out from the outer casing.

In some embodiments, for each of the plurality of kit pages, the right page region includes edges or side surfaces that are oriented orthogonal to a remainder of the right page region, so as to form a box-like structure on the right page region.

In some embodiments, at least some of the plurality of pockets are formed from a puncture-resistant material.

In some embodiments, the right casing region includes a gripping material on a bottom surface thereof configured to secure the outer casing to an external surface, allowing the left casing region to be unfolded away from the right casing region in a page-turning motion.

In some embodiments, the medical device kit includes a fastening device configured to secure the left casing region to the right casing region when the left casing region is folded over the right casing region.

DESCRIPTION OF THE INVENTION

Figure 1:
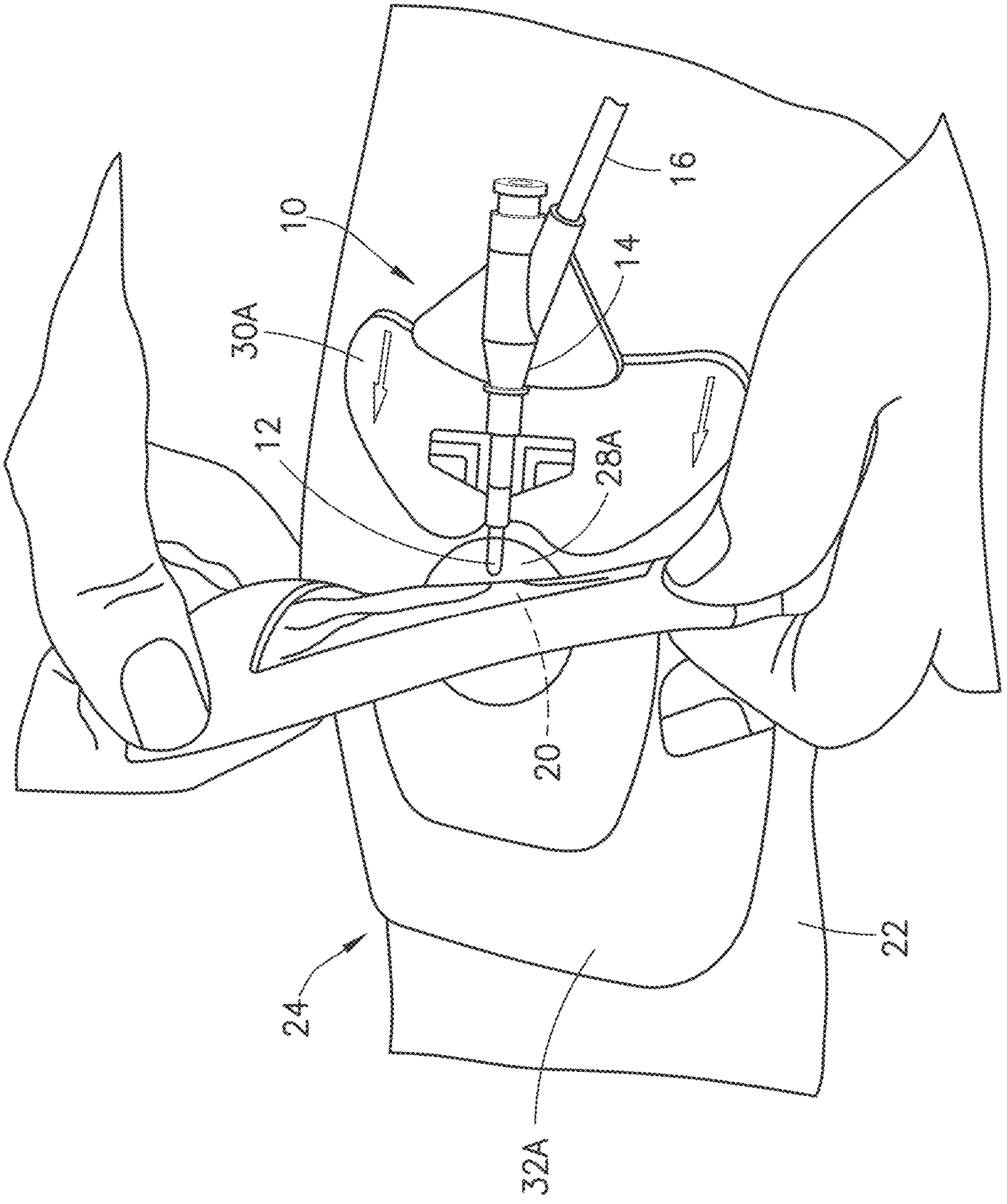
FIG. 1 is a perspective view of a catheter inserted into a body of a patient, exhibiting one example environment with which embodiments of the disclosure can be practiced.

The following description is provided to enable those skilled in the art to make and use the described embodiments contemplated for carrying out the invention. Various modifications, equivalents, variations, and alternatives, however, will remain readily apparent to those skilled in the art. Any and all such modifications, equivalents, variations, and alternatives are intended to fall within the spirit and scope of the present invention.

For purposes of the description hereinafter, the terms "upper", "lower", "right", "left", "vertical", "horizontal", "top", "bottom", "lateral", "longitudinal", and derivatives thereof shall relate to the invention as it is oriented in the drawing figures. However, it is to be understood that the invention may assume various alternative variations, except where expressly specified to the contrary. It is also to be understood that the specific devices illustrated in the attached drawings, and described in the following specification, are simply exemplary embodiments of the invention. Hence, specific dimensions and other physical characteristics related to the embodiments disclosed herein are not to be considered as limiting.

The terms "first", "second", and the like are not intended to refer to any particular order or chronology, but refer to different conditions, properties, or elements.

As used herein, "at least one of" is synonymous with "one or more of." For example, the phrase "at least one of A, B, and C" means any one of A, B, or C, or any combination of any two or more of A, B, or C. For example, "at least one of A, B, and C" includes one or more of A alone; or one or more of B alone; or one or more of C alone; or one or more of A and one or more of B; or one or more of A and one or more of C; or one or more of B and one or more of C; or one or more of all of A, B, and C.

Provided herein are medical device kits for use in placing, maintaining, altering, and/or removing medical devices in, on, and/or from the body of a patient. Such medical device kits can include a plurality of medical devices and supplies for use in the placement/maintenance procedure. In accordance with present embodiments, the medical device kit can include various organizational and waste disposal features to assist the clinician or user performing the particular procedure. These various features are outlined in further detail below.

Reference is first made to FIG. 1, which depicts a catheter 10 including a catheter tube 12 inserted transcutaneously through a skin 22 of a patient 24 via an insertion site 20. Though the catheter 10 shown here is a peripheral intravenous catheter (PIVC), various other catheters and medical devices can benefit from the principles and features described below. Examples of other catheters and elongate tubular devices include dialysis catheters, Foley and urinary catheters, feeding tubes, balloon catheters, peripheral intravenous (PIVs), etc. Vascular and other types of access ports are further examples of medical devices that may be employed. Also, though shown here inserted into the arm of the patient 24, the catheter 10 or other medical device can be disposed in other areas of the body of the patient, not only transcutaneously, but topically or subcutaneously as well. In another embodiment, the medical device is not connected to or in contact with the patient's body. Thus, these and other modifications are therefore contemplated.

FIG. 1 further shows that the catheter 10 includes an adapter 14 and one or more fluid conduits 16 that operably connect, via the adapter 14, to a corresponding number of lumens defined by the catheter tube 12. An antimicrobial/hemostatic patch 28A, is disposed about the catheter tube 12 at the insertion site 20, and a catheter securement device 30A is removably attached to the patient skin 22 so as to removably attach to and secure the adapter 14 of the catheter. An adhesive dressing 32A is adhesively and removably positioned so as to cover the external portion of the catheter 10, the patch 28A, and the securement device 30A and isolate the insertion site 20 and protect it from contamination. The patch 28A, the securement device 30A, and the adhesive dressing 32A are collectively referred to herein as a "dressing assembly" or "dressing," though it is appreciated that more or fewer components can be included in the assembly.

As shown in FIG. 1, it is periodically necessary to change the current/existing dressing assembly of the indwelling catheter 10 and replace it with a new dressing assembly. As such, FIG. 1 shows the patch 28A, the securement device 30A, and the adhesive dressing 32A as old components needing to be changed, with FIG. 1 further showing the old adhesive dressing 32A being removed from the patient skin 22 by a clinician. Additionally, it is recognized that additional procedures related to use of an indwelling catheter 10 may need be performed, including flushing of the catheter 10, removal of the catheter 10, and/or insertion of a catheter 10 (i.e., an initial insertion of the catheter 10 or removal of an existing catheter and replacement with a new catheter 10).

FIGS. 2-5 show a medical device kit ("kit") 50 according to one embodiment, which can be used in a procedure to replace the old dressing assembly with a new dressing assembly for an indwelling catheter, such as the catheter 10 shown in FIG. 1. In other embodiments, and as indicated above, the kit 50 can be used in a procedure to flush an indwelling catheter, remove an indwelling catheter, or insert a new indwelling catheter. The kit 50 of FIGS. 2-5 is thus referred to in the present embodiment as a "catheter kit" or "catheter maintenance kit" and includes various components needed to remove or insert a catheter or perform catheter maintenance (dressing change procedure, catheter flushing procedure, etc.), though it is appreciated that the kit can be configured for one or more of a variety of procedures involving a medical device. The discussion to follow is therefore illustrative and is not to be considered as limiting.

Figure 2:
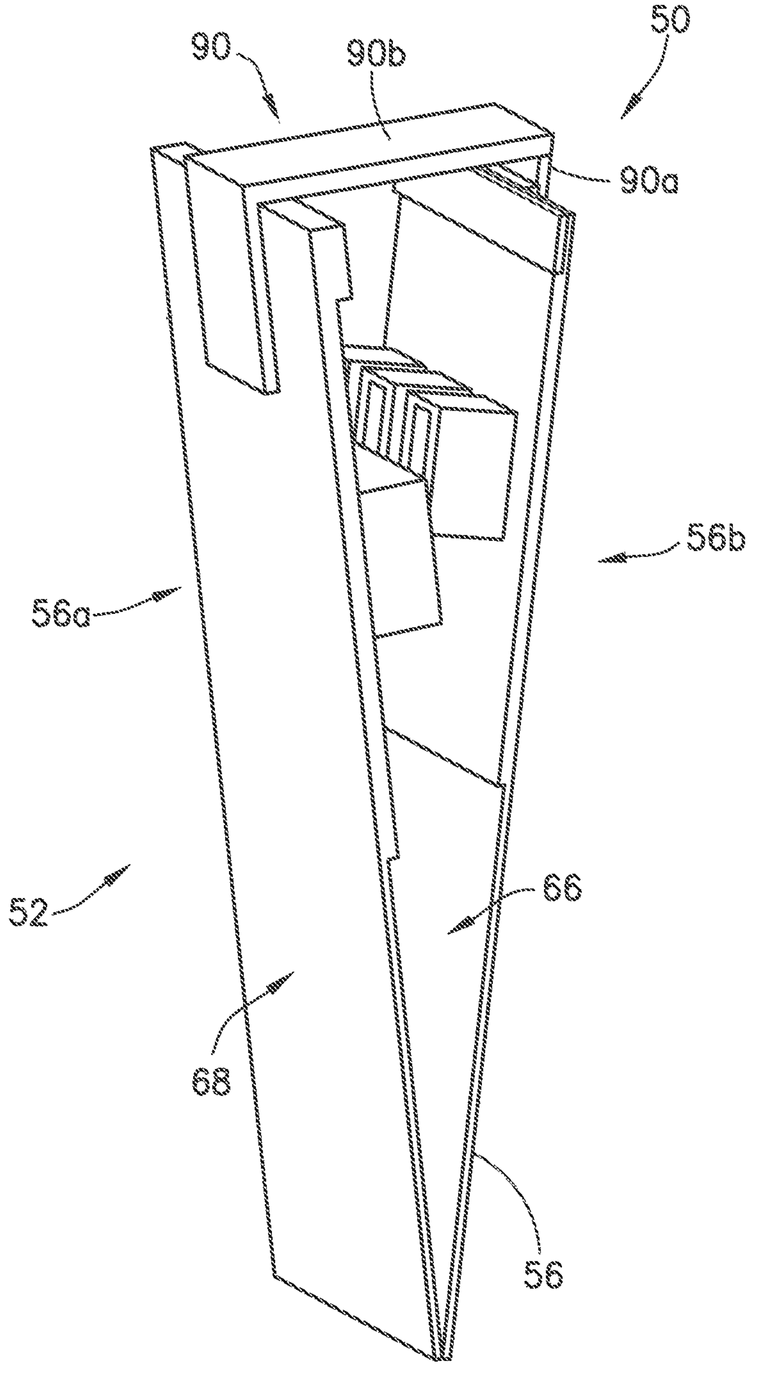
FIG. 2 is a perspective view of a medical device kit, shown in a storage configuration, according to an embodiment described herein.
Figure 3:
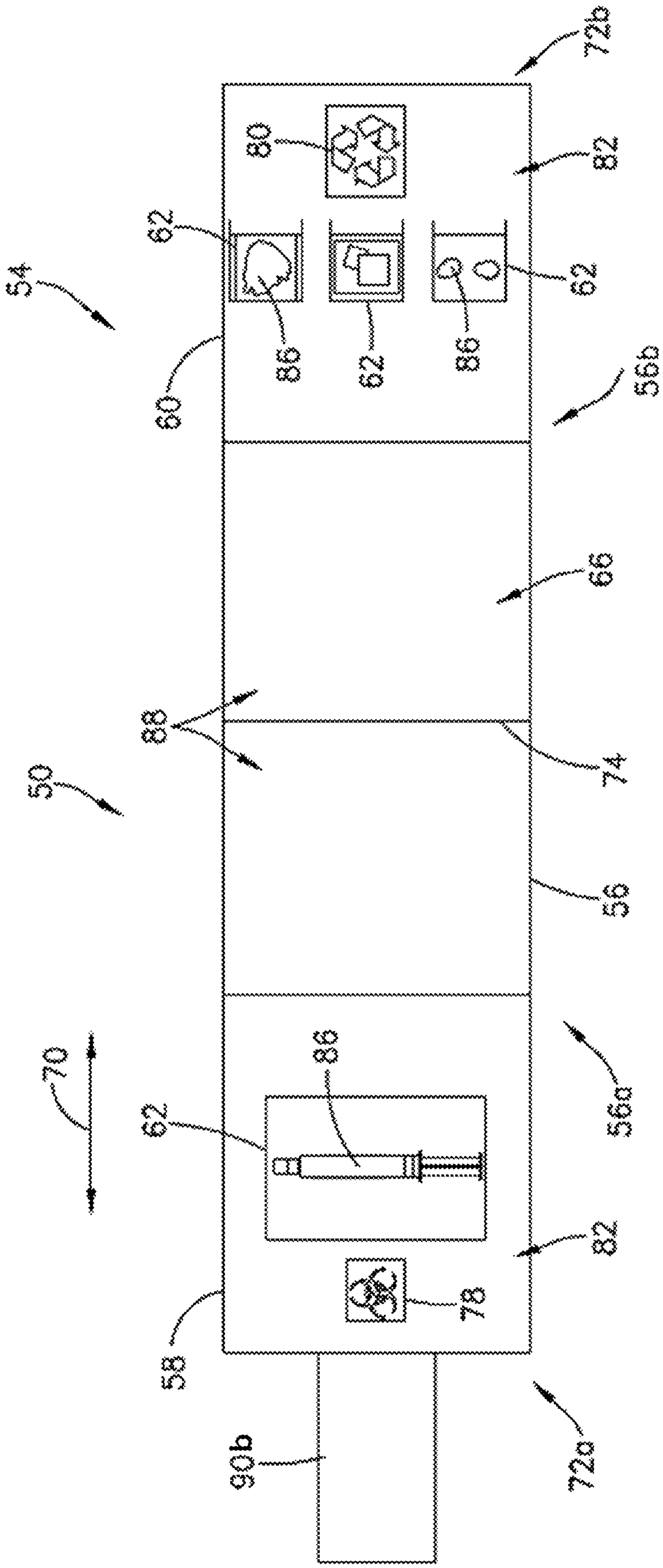
FIG. 3 is a top view of the medical device kit of FIG. 2, shown in a usage configuration.

As shown in FIGS. 2 and 3, the kit 50 is transformable between a storage configuration 52 (FIG. 2) and a usage configuration 54 (FIG. 3). In the storage configuration 52, the kit 50 may securably retain therein the various medical devices and supplies contained in the kit 50 and allow for a clinician to easily transport the kit 50. When a clinician desires to access the kit 50 to use the contents thereof for performing a desired treatment or procedure, the kit 50 may be transformed from the storage configuration 52 to the usage configuration 54 to provide access to the medical devices and supplies included in the kit 50.

The kit 50 generally includes a base sheet 56, first and second waste bins 58, 60, a plurality of pockets 62, and a plurality of fastening devices 90. FIG. 4 depicts various details of the base sheet 56, configured according to one embodiment. The base sheet 56 may be employed, in one embodiment, to serve as a platform for supporting the components of the kit 50 in the storage and usage configurations 52, 54, as will be described below. Additionally, the base sheet 56 is configured to serve as a sterile surface/platform or "prep area" for the medical devices and supplies used in the treatment/procedure to be performed, such as a changing of the dressing assembly for the catheter 10.

In greater detail, the base sheet 56 is configured as a substantially flat, flexible, and sheet or body. The base sheet 56 may thus be formed of a spunbond-meltblown-spunbond ("SMS") nonwoven fabric or other suitable material/fabric that, in some embodiments, is a waterproof nonwoven fabric. The base sheet 56 includes an inner surface 66 and an opposite outer surface 68, with the inner and outer surfaces 66, 68 being understood as the surfaces that face inward (inner surface 66) and outward (outer surface 68) when the kit 50 is in a folded, storage configuration 52 and that face upward (inner surface 66) and downward (outer surface 68) when the kit 50 is in an unfolded, usage configuration 54. The base sheet 56 is generally divided into a first base portion 56*a* and a second base portion 56*b* that, as shown in FIG. 3, are generally positioned on opposing ends 72*a* 72*b* of the base sheet 56 along a lengthwise direction 70. In some embodiments, the base sheet 56 includes a tear line 74 formed along a centerline of the base sheet 56, between the first base portion 56*a* and the second base portion 56*b*. The tear line 74 allows for the first base portion 56*a* to be separated from the second base portion 56*b* along the tear line 74, when use of the kit 50 is completed and it is to be disposed of, as will be explained in detail later.

Figure 4A:
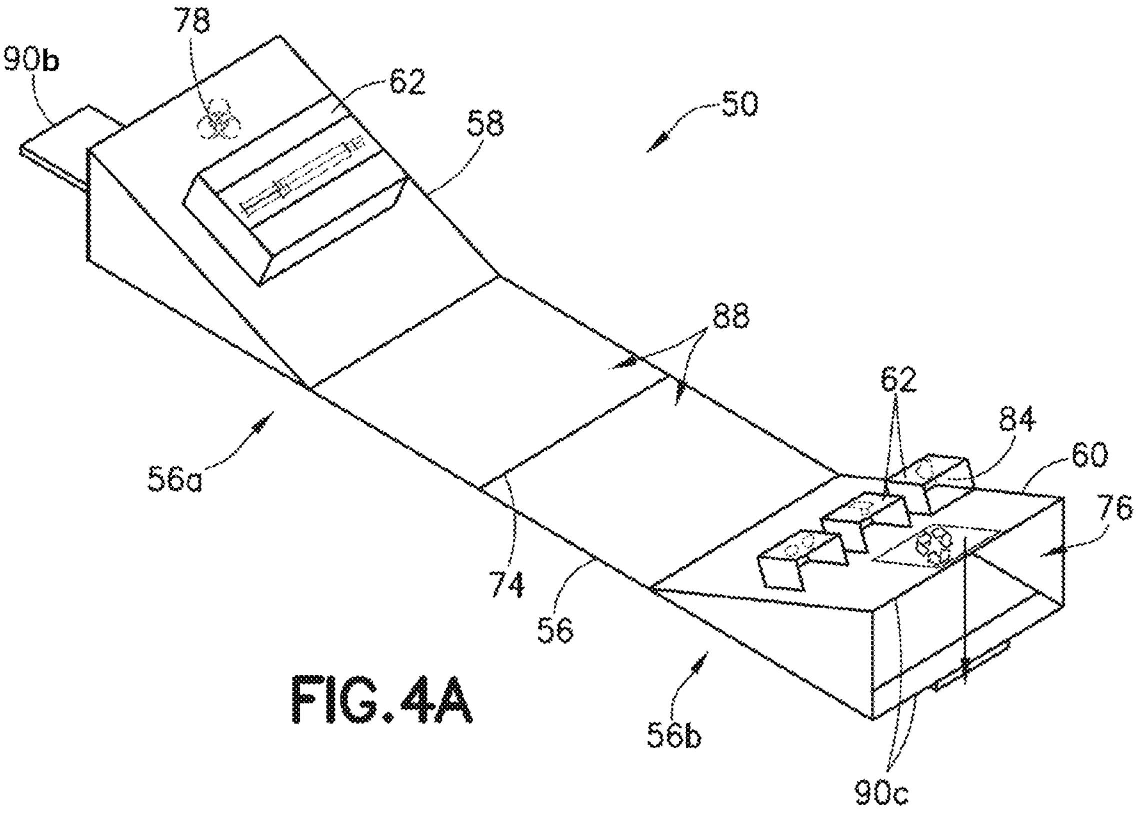
FIG. 4A is a right-hand perspective view of the medical device kit of FIG. 3, illustrating open waste bins thereof.
Figure 4B:
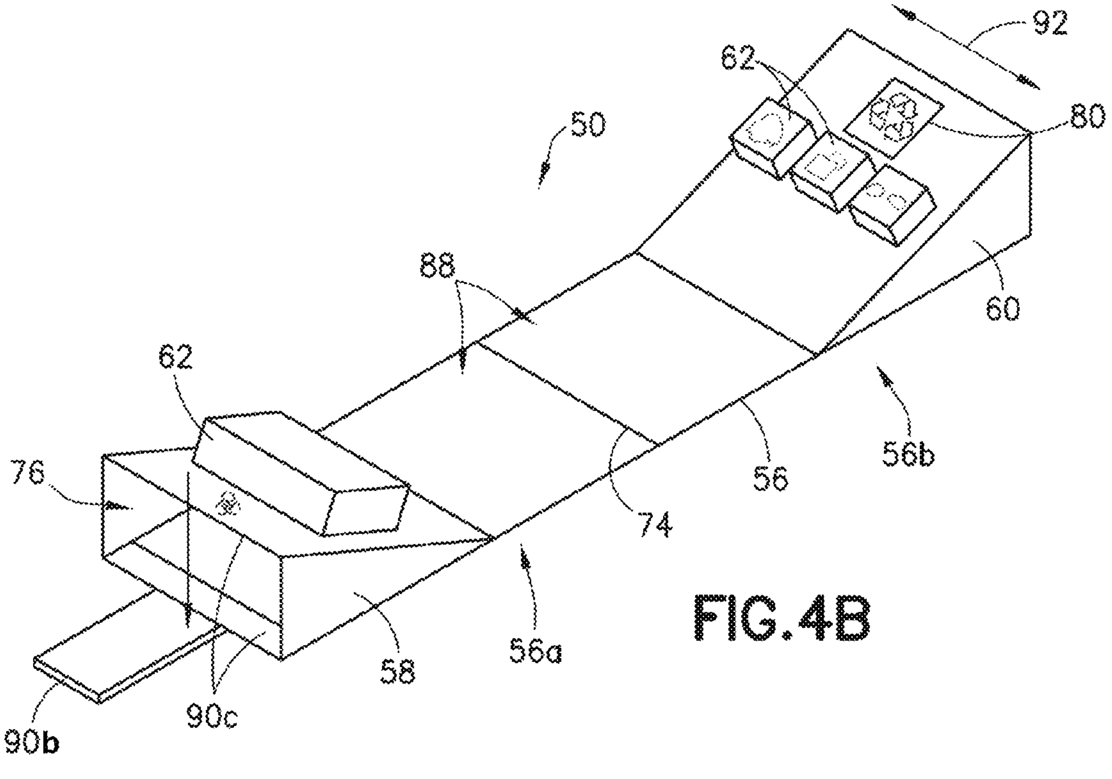
FIG. 4B is a left-hand perspective view of the medical device kit of FIG. 3, illustrating open waste bins thereof.

The inner surface 66 of the base sheet 56 includes a first waste bin 58 and a second waste bin 60 provided thereon, with the first waste bin 58 being provided on the first base portion 56*a* and the second waste bin 60 being provided on the second base portion 56*b*. In some embodiments, the waste bins 58, 60 are formed of a sheet or sheets of flexible material, such as a SMS nonwoven fabric like the base sheet 56, or another suitable material/fabric. In the present embodiment, and as best shown in FIGS. 4A and 4B, the material defining each of the first waste bin 58 and the second waste bin 60 is a single, shaped piece of nonwoven material that is secured to the inner surface 66 of the base sheet 56. According to embodiments, the material defining each of the first waste bin 58 and the second waste bin 60 may be secured to the base sheet 56 via stitching, ultrasonic welding, adhesive, or another suitable fixation mode, as examples. As shown in FIGS. 4A and 4B, the material defining each of the first waste bin 58 and the second waste bin 60 is secured to the base sheet 56 along the bottom and sides of the bin—with the "top" of each bin being left unsecured and open. The openings 76 of the first waste bin 58 and the second waste bin 60 are thus oriented or directed toward opposing first and second ends of the base sheet 56.

In some embodiments, the first waste bin 58 and the second waste bin 60 may be differentiated in their appearance, so as to indicate to a clinician that one of the bins is to be used to receive and store non-hazardous/general packaging waste and the other of the bins is to be used to receive and store hazardous medical waste. In some embodiments, the first waste bin 58 and the second waste bin 60 may be labeled or color coded to differentiate them from each other, with the illustrated embodiment showing that the first waste bin 58 is marked with a biohazard label 78 and the second waste bin 60 is marked with a non-hazardous/general label 80. Thus, after medical devices and supplies included in the kit 50 are used by the clinician during the procedure, the remaining medical waste may be easily placed into the appropriate waste bin 58, 60, therefore keeping the work area free of medical waste.

A plurality of pockets 62 are included in the kit 50 for receiving therein the medical devices and supplies that are to be used during the procedure to be performed by the clinician, such as removing the old dressing assembly from the catheter 10. The pockets 62 may be positioned on one or both of the first waste bin 58 and the second waste bin 60, on an outward facing surface 82 thereof (i.e., facing away from base sheet 56), with the illustrated embodiment showing pockets 62 being provided on both the first waste bin 58 and the second waste bin 60. In some embodiments, the pockets 62 are formed of a polymeric material (e.g., polypropylene), with each pocket 62 shaped to form a receptacle therein having an opening 84 on one side. The pockets 62 may be secured to the waste bins 58, 60 via use of an adhesive, with the adhesive optionally allowing for the pockets 62 to be removed from the waste bins 58, 60 if desired by the clinician, as will explained in more detail below.

As previously indicated, each of the pockets 62 is sized to receive therein medical devices and supplies (generally indicated as 86) that are to be used during the procedure to be performed by the clinician. According to embodiments, the devices/supplies 86 may include sterile gloves, alcohol wipes, syringes, gauze, sutures, tape, dressings, disinfecting caps, swab sticks, tourniquets, securement devices, hemostatic agents, and/or anticoagulants, as examples. The illustrated embodiment shows pocket 62 positioned on first waste bin 58 as receiving a Posiflush Kodiak syringe therein and pockets 62 on second waste bin 60 as receiving sterile gloves, an alcohol wipe, and disinfecting caps. The components could vary in number, type, position, etc., in other embodiments, however. Similarly, the size, shape, number, and configuration of the pockets 62 themselves can vary from what is shown and described herein. In the present embodiment, the kit 50 includes four (4) pockets 62, though other numbers of pockets 62 can be included.

According to an embodiment, when in the usage configuration 54, the kit 50 is configured to provide a sterile surface/platform or "prep area" 88 in and on which the medical devices and supplies 86 included in the kit 50 may be placed and arranged by the clinician upon being removed from the pockets. The prep area 88 is provided by the inner surface 66 of the base sheet 56 on an area thereof between the first waste bin 58 and the second waste bin 60. The base sheet 56 (and, more generally, kit 50) may be subjected to sterilization procedures sufficient to render the inner surface 66 of the base sheet 56 a sterile field onto which the devices/supplies 86 may be laid (with the devices/supplies 86 also sterilized). In another embodiment, the inner surface 66 of the base sheet 56 is configured as a clean surface instead of a sterile surface, e.g., the inner surface 66 is suitable for a procedure where only a clean field is required, as opposed to a sterile field. In other embodiments, the inner surface 66 of the base sheet 56 can be configured as other field types, including aseptic, in one embodiment.

A plurality of fastening devices 90 are also provided on kit 50 to secure and/or close components thereof. According to some embodiments, the fastening devices 90 provided on kit 50 are in the form of hook-and-loop fasteners (e.g., Velcro™ strips) that provide for a selective engagement and disengagement of components from one another during use of the kit. However, while fastening devices 90 are here after referenced as hook-and-loop fasteners 90, it is recognized that other fastening devices 90 may instead be utilized in kit 50, such as snap-fit fasteners, adhesive fasteners, and the like.

In one embodiment, the hook-and-loop fasteners 90 may include base sheet hook-and-loop fasteners **90*a* provided on the kit 50 to secure the first base portion 56*a* to the second base portion 56*b* when the kit 50 is in the storage configuration 52 (FIG. 2). The base sheet hook-and-loop fasteners 90*a* may be provided on outer surface 68 of the base sheet 56, adjacent to the opposing ends 72*a*, 72*b* of the base sheet 56, with a connecting hook-and-loop fastener 90*b* spanning between the base sheet hook-and-loop fasteners 90*a* to secure the first base portion 56*a* to the second base portion 56*b* when the kit 50 is in the storage configuration 52**.

In one embodiment, the hook-and-loop fasteners 90 may also include bin hook-and-loop fasteners **90*c* (see FIGS. 4A and 4B) that are provided in proximity to the openings 76 of first and second waste bins 58, 60, to enable the first waste bin 58 and the second waste bin 60 to be to selectively sealed shut. In one embodiment, bin hook-and-loop fasteners 90*c* may be provided adjacent the opening 76 of each of the first and second waste bins 58, 60, with a hook-and-loop fastener strip 90*c* on the inward facing surface of each of the waste bins 58, 60 and another hook-and-loop fastener strip 90*c* on the inner surface 66 of the base sheet 56. For each waste bin 58, 60, the hook-and-loop fastener strips 90*c* on the inward facing surface of the sheet forming the waste bin 58, 60 and on the inner surface 66 of the base sheet 56 are aligned with each other, with the strips 90*c* oriented in a width-wise direction 92 such that, when mated together, the opening 76 of each waste bin 58, 60** is effectively sealed shut to secure medical waste therein.

Following now is a work flow describing a plurality of steps to be followed by a clinician when using the kit 50 to perform a desired medical treatment or procedure. As previously described, exemplary treatments/procedures for which the kit 50 may be used include changing a catheter dressing assembly flushing an indwelling catheter, removing an indwelling catheter, or inserting a new indwelling catheter, as non-limiting examples.

In an initial step, a clinician may receive the kit 50 in its storage configuration 52 (FIG. 2) and proceed to actuate a fastening device 90 thereon to unlock the kit 50 and allow it to transform from the folded storage configuration 52 to an unfolded usage configuration 54 (FIG. 3). In one embodiment, actuating the fastening device 90 includes unhooking or releasing mating hook-and-loop fasteners from one another (e.g., removing connecting hook-and-loop fastener **90*b* from base sheet hook-and-loop fasteners 90*a*) to allow the first base portion 56*a* to be moved away from the second base portion 56*b***.

As shown in FIG. 3 and FIGS. 4A and 4B, upon the kit 50 being moved into its usage configuration 54, the base sheet 56 is in a flat arrangement and the clinician has access to the medical devices and supplies 86 secured within pockets 62. The clinician may remove the desired devices/supplies 86 and prepare and arrange them as desired in the prep area 88 provided on base sheet 56—between the first waste bin 58 and the second waste bin 60.

Figure 5A:
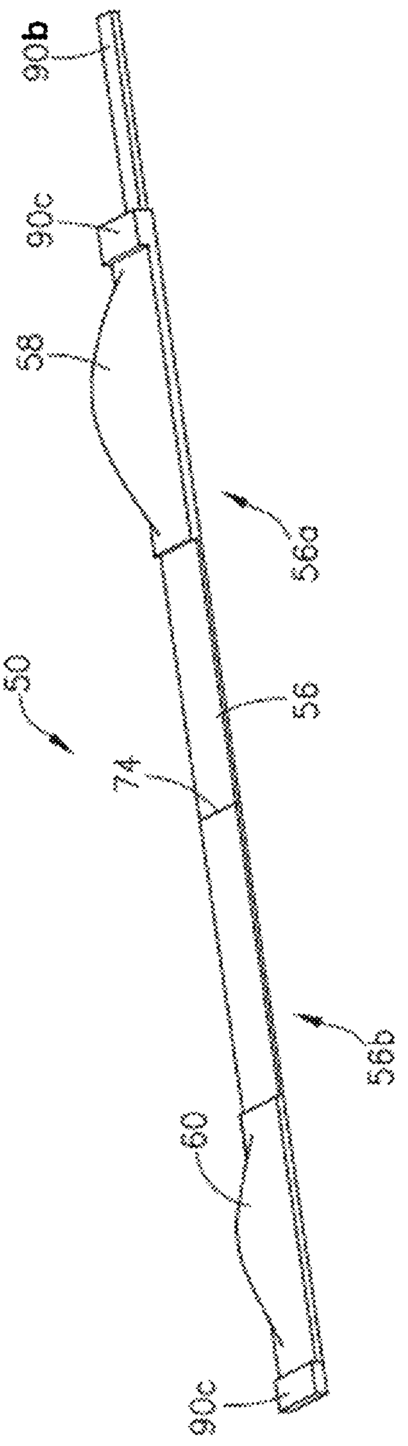
FIG. 5A is a front perspective view of the medical device kit of FIG. 3, illustrating sealed waste bins thereof.

Once the clinician has finished using a particular medical device or supply as part of the treatment/procedure being performed, the clinician may transfer the used device/supply (i.e., medical waste) into one of the waste bins 58, 60 provided in kit 50, as shown in FIG. 5A. According to embodiments, the clinician may dispose of any hazardous medical waste (e.g., a used syringe) into the (first) waste bin 58 marked with a biohazard label 78 and may dispose of medical device/product packaging into the (second) waste bin 60 marked with a non-hazardous/general label 80.

Figure 5B:
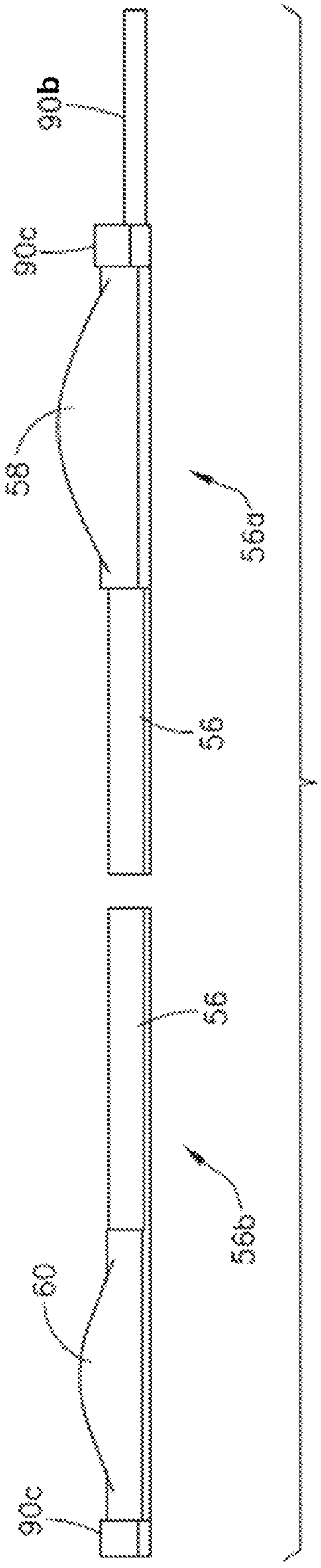
FIG. 5B is a front perspective view of the medical device kit of FIG. 5, illustrating a first base portion torn apart from a second base portion.

Upon medical waste from the used devices/supplies being placed into their appropriate waste bins 58, 60 on kit 50, the clinician may seal the respective waste bins 58, 60, such as via the bin hook-and-loop fasteners 90*c* provided adjacent the opening 76 of each of the first and second waste bins 58, 60, as shown in FIG. 5A. With the waste bins 58, 60 sealed, the clinician may then tear the base sheet 56 along the tear line 74, as shown in FIG. 5B, thereby separating the first base portion 56*a* (including the first waste bin 58 thereon) from the second base portion 56*b* (including the second waste bin 60 thereon). The clinician may then appropriately dispose of the hazardous medical waste in the first waste bin 58 and the non-hazardous/general medical waste in the second waste bin 60 by depositing them into larger marked waste containers present in the healthcare facility.

Figure 6:
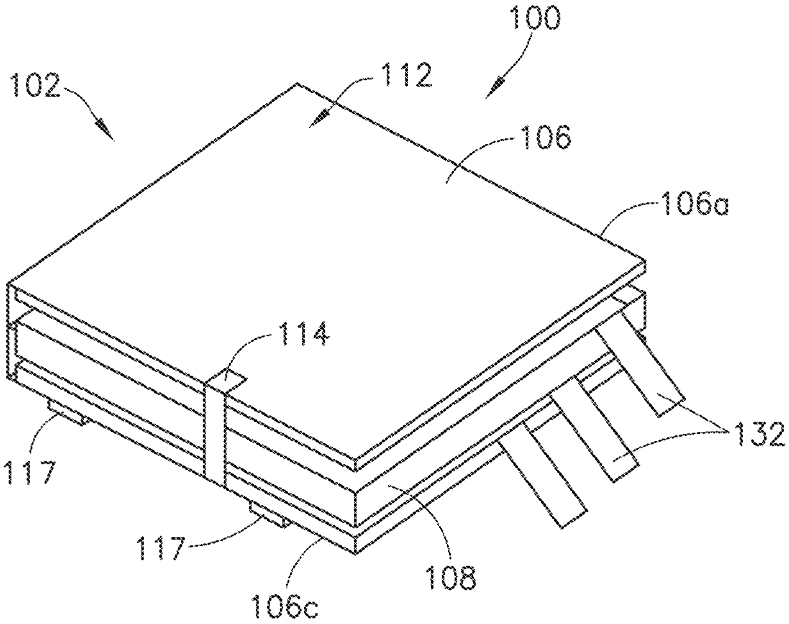
FIG. 6 is a perspective view of a medical device kit, shown in a storage configuration, according to another embodiment described herein.
Figure 7:
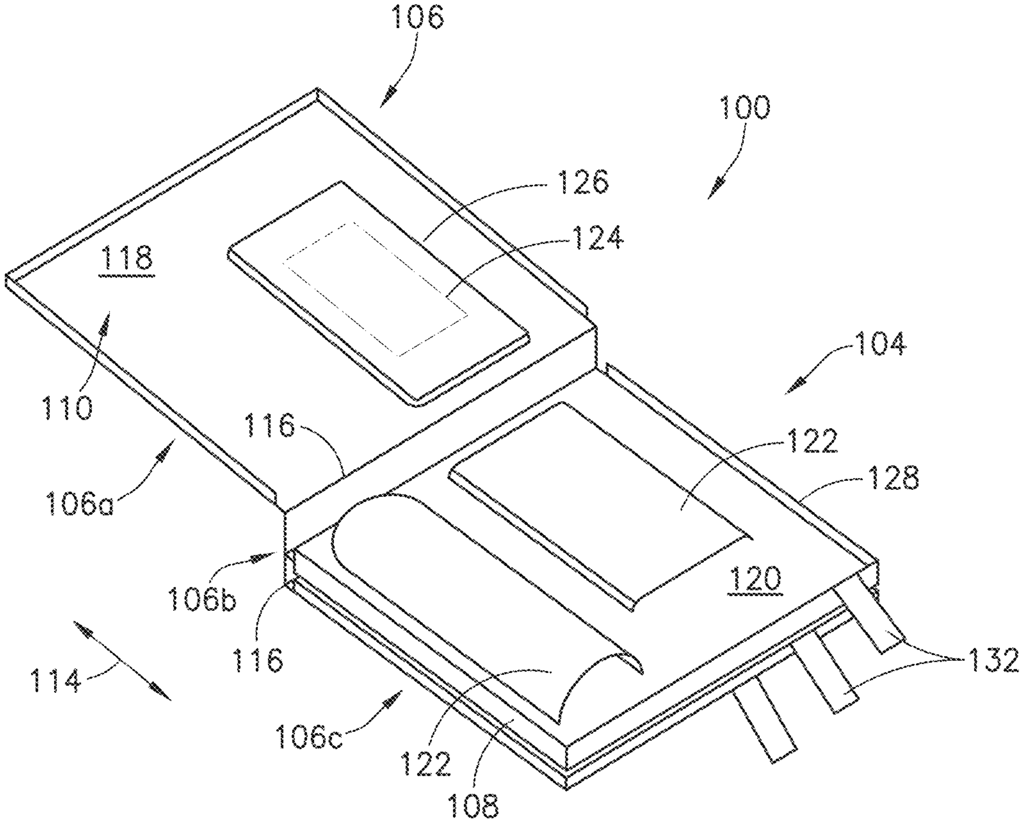
FIG. 7 is a perspective view of the medical device kit of FIG. 6, shown in a usage configuration.

Referring now to FIGS. 6-13, a medical device kit ("kit") 100 is shown according to another embodiment. Again, the kit 100 is described here as catheter kit that can be used in a procedure to replace an old dressing assembly for an indwelling catheter, flush an indwelling catheter, remove an indwelling catheter, or insert a new indwelling catheter. The kit 100 of FIGS. 6 and 7 is thus referred to in the present embodiment as a "catheter kit" and includes various components needed to remove or insert a catheter or perform catheter maintenance (dressing change procedure, catheter flushing procedure, etc.), though it is appreciated that the kit 100 can be configured for one or more of a variety of procedures involving a medical device. The discussion to follow is therefore illustrative and is not to be considered as limiting.

As shown in FIGS. 6 and 7, the kit 100 is transformable between a storage configuration 102 (FIG. 6) and a usage configuration 104 (FIG. 7). In the storage configuration, the kit 100 may securably retain therein the various medical devices and supplies contained therein and allow for a clinician to easily transport the kit 100. When a clinician desires to access the kit 100 to use the contents thereof for performing a desired treatment or procedure, the kit 100 may be transformed from the storage configuration 102 to the usage configuration 104 to provide access to the medical devices and supplies included in the kit 100.

The kit 100 generally includes an outer casing 106 and a plurality of kit pages 108 contained within the outer casing 106. In the context of the storage and usage configurations 102, 104 described above, the outer casing 106 may generally enclose the kit pages 108 when the kit 100 is in the storage configuration 102, with the outer casing 106 folded over on itself, while the outer casing 106 may allow access to the kit pages 108 when the when the outer casing 106 is opened to the usage configuration 104.

FIGS. 6 and 7 depict various details of the outer casing 106, configured according to one embodiment. The outer casing 106 is configured as a semi-rigid and sheet or body. The outer casing 106 may thus be formed of a corrugated fiberboard, paperboard, mat board, or other suitable material that provides structure and rigidity to the kit 100. The outer casing 106 includes an inner surface 110 and an opposite outer surface 112, with the inner and outer surfaces 110, 112 being understood as the surfaces that face inward (inner surface 110) and outward (outer surface 112) when the kit 100 is in a folded, storage configuration 102 and that face upward (inner surface 110) and downward (outer surface 112) when the kit 100 is in an unfolded, usage configuration 104. The outer casing 106 is further divided into a left casing region 106*a*, a center casing region 106*b*, and a right casing region 106*c* that, as shown in FIG. 3A, are generally arranged along a lengthwise direction 114. The center casing region 106*b* is divided from the left and right casing region 106*cs* by fold lines 116, with the fold lines 116 allowing for the left casing region 106*a* to be folded over the right casing region 106*c*. The outer casing 106 (and kit in general) can therefore be considered a book-type structure, with the outer casing 106 including the plurality of kit pages 108 therein and the center casing region 106*b* providing a binding or binding region for the kit pages 108.

In some embodiments, a fastening device 114 may be provided on the outer casing 106 to secure the left casing region 106*a* to the right casing region 106*c* when the left casing region 106*a* is folded over the right casing region 106*c* in the storage configuration 102. As one example, the fastening device 114 provided on kit 100 is an adhesive strip that secures the left casing region 106*a* to the right casing region 106*c* when the kit 100 is in the storage configuration 102 (FIG. 6). In other non-limiting embodiments, the fastening device 114 provided on kit 100 may be in the form of a hook-and-loop fastener or snap-type closure.

In some embodiments, the right casing region 106*c* of outer casing 106 includes a gripping material 117 on the outer surface 112 thereof. The gripping material 117 may be configured to secure the outer casing 106 to an external surface on which the kit 100 is placed during use, thus holding the kit 100 in place and allowing the left casing region 106*a* to be more easily unfolded away from the right casing region 106*c* in a page-turning motion. According to embodiments, the gripping material 117 may be an arrangement of high friction elements (e.g., rubberized grips) or a double sided tape/adhesive element provided on the outer surface 112 of the right casing region 106*c*, as examples.

The kit pages 108 included in the kit 100 may be structurally similar to the outer casing 106, and may thus be formed of a corrugated fiberboard, paperboard, mat board, or other suitable material that is able to support the medical devices or supplies provided in the kit 100. The kit pages 108 are secured to the outer casing 106 in the center casing region 106*b* so that the kit pages 108 are contained within the outer casing 106 when the left casing region 106*a* is folded over the right casing region 106*c*. The kit pages 108 may be attached to the center casing region 106*b* via a binding of a suitable type, such as via threads or fibers that secure the kit pages 108 to the outer casing 106. The number of kit pages 108 or "layers" included in the kit 100 will vary based on the treatment/procedure to be performed with the kit 100, with a 3-layer kit, 4-layer kit, or kit 100 with a still greater number of layers being possible for some catheter kits, as an example.

Figure 8:
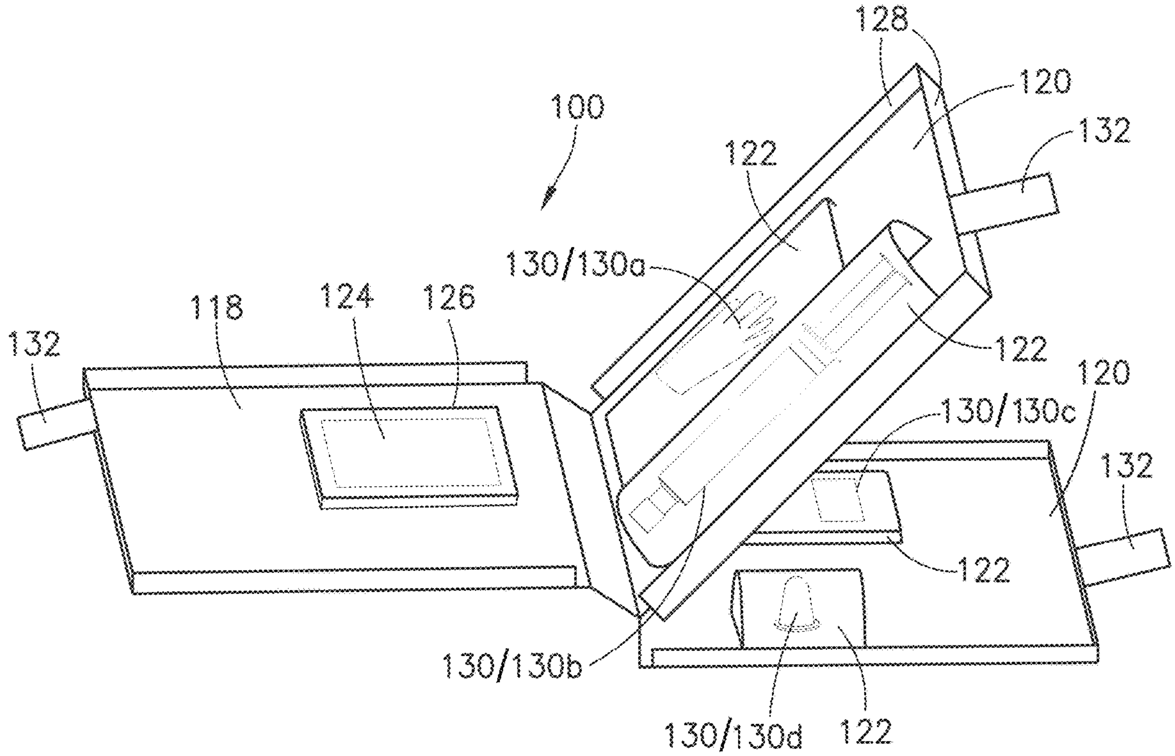
FIG. 8 is a perspective view of the medical device kit of FIG. 7, illustrating kit pages of the medical device kit.

As best shown in FIGS. 7 and 8, each of the kit pages 108 may generally be characterized as including a left page region 118 and a right page region 120. The right page region 120 of each kit page includes one or more pockets 122 thereon each configured to store medical devices or supplies therein that are to be used during the procedure to be performed by the clinician, while the left page region 118 includes instructions 124 thereon (e.g., a slip of paper instructions, which may be provided in a sleeve 126) regarding use of the medical device or supplies stored in the pocket(s) on the associated right page region 120 for a treatment/procedure step (or steps) to be performed with those devices/supplies. For at least some of the kit pages 108, the right page region 120 may have edges or side surfaces 128 that are oriented orthogonal to the remainder of the page, with the orthogonally oriented edges 128 thus forming a box-like structure on the right page region 120 that helps to contain the contents of the right page region 120 (i.e., of devices/supplies included in the pockets 122) when the kit 100 is in its storage configuration 102, so as to help secure the contents of the kit 100. In some embodiments, it is recognized that the inner surface 110 of the left casing region 106*a* may serve as the left page region 118 of a "first kit page" in the kit 100.

Regarding the right page region 120, each of the pockets 122 is sized to receive therein medical devices or supplies 130 that are to be used during the procedure to be performed by the clinician, as shown in FIG. 8 as an example. According to embodiments, the devices/supplies 130 may include sterile gloves, alcohol wipes, syringes, gauze, sutures, tape, dressings, disinfecting caps, swab sticks, tourniquets, securement devices, hemostatic agents, and/or anticoagulants, as examples. The size, shape, number, configuration and construction of the pockets 122 themselves can vary based on the devices/supplies 130 to be stored therein. As one example, the material from which the pockets 122 is formed can vary based on the device or supply 130 that is stored in the pocket. For those pockets 122 designed to store supplies such as sterile gloves, alcohol wipes, gauze, sutures, tape, or dressings, as examples, the pockets 122 may be formed of a polymeric material (e.g., polypropylene). For those pockets 122 designed to store syringes or other devices/supplies with sharp or pointed features, the pockets 122 may be formed from a puncture-resistant material such as an elastomer or thermoplastic composite laminate, e.g., glass fiber mat coated with nanosilica and sandwiched between two layers of thermoplastic elastomer (TPE) film.

According to embodiments, the kit pages 108 are arranged sequentially in the kit 100 according to an order in which the medical devices and supplies 130 included therein are to be used in defined steps of the treatment/procedure to be performed by the clinician. FIG. 8 illustrates an example of a 3-layer kit for flushing of an indwelling catheter (e.g., peripheral intravenous catheter (PIVC), peripherally inserted central catheter (PICC), or central venous catheter (CVC)) that includes two arranged sequentially kit pages 108. A first kit page 108 of the kit 100 corresponds to a first step (or group of steps) in the treatment/procedure and includes a pair of pockets 122 provided on the right page region 120, with a first pocket 122 having sterile gloves 130*a* therein and the second pocket 122 having a Posiflush Kodiak syringe 130*b* therein. The corresponding left page region 118 of the first kit page includes instructions 124 thereon, which may be in the form of textual or symbolic instructions that instruct the clinician regarding the order and manner in which to use the gloves 130*a* and syringe 130*b*. A second kit page 108 of the kit 100 corresponds to a second step (or group of steps) in the treatment/procedure and includes a pair of pockets 122 provided on the right page region 120, with a first pocket 122 having alcohol wipes 130*c* therein and the second pocket 122 having a male/female universal cap 130*d* therein. The corresponding left page region 118 of the second kit page 108 includes instructions 124 thereon, which may be in the form of textual or symbolic instructions that instruct the clinician regarding the order and manner in which to use the wipes 130*c* and cap 130*d*.

Figure 9:
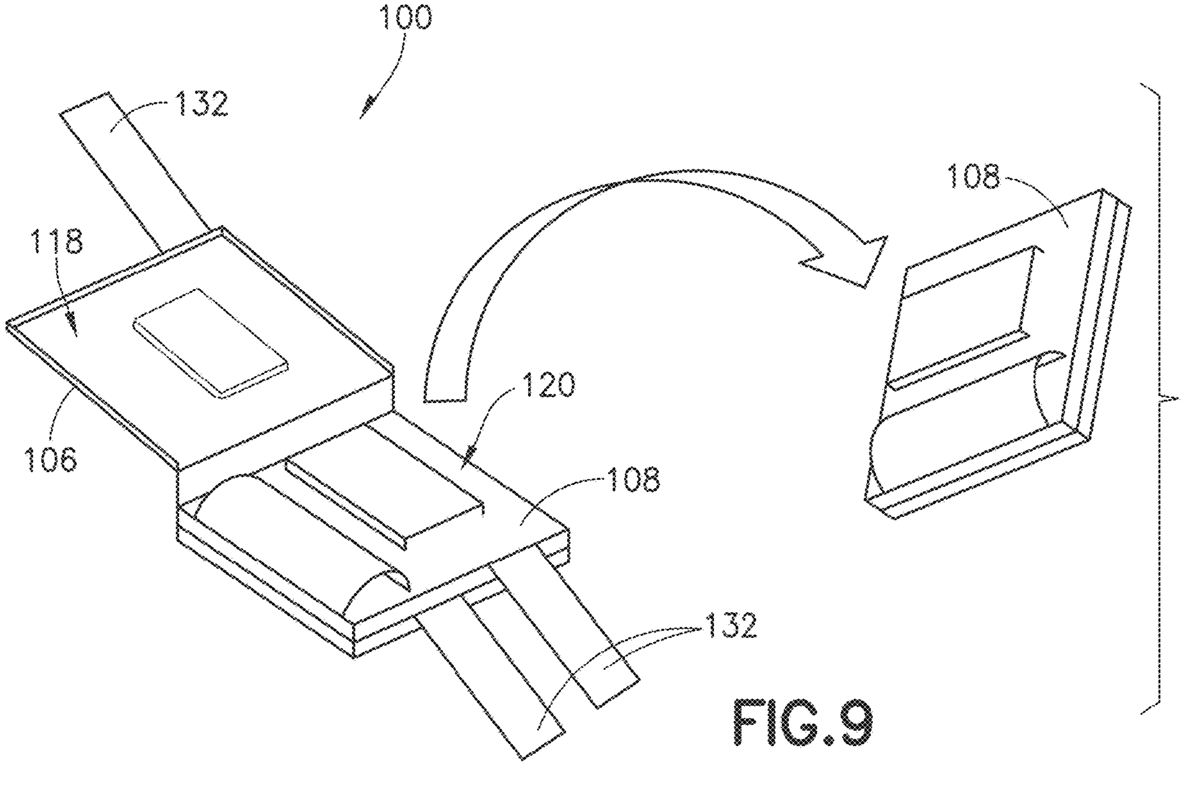
FIG. 9 is a perspective view of the medical device kit of FIG. 7, illustrating a kit page being torn out from the medical device kit.
Figure 10:
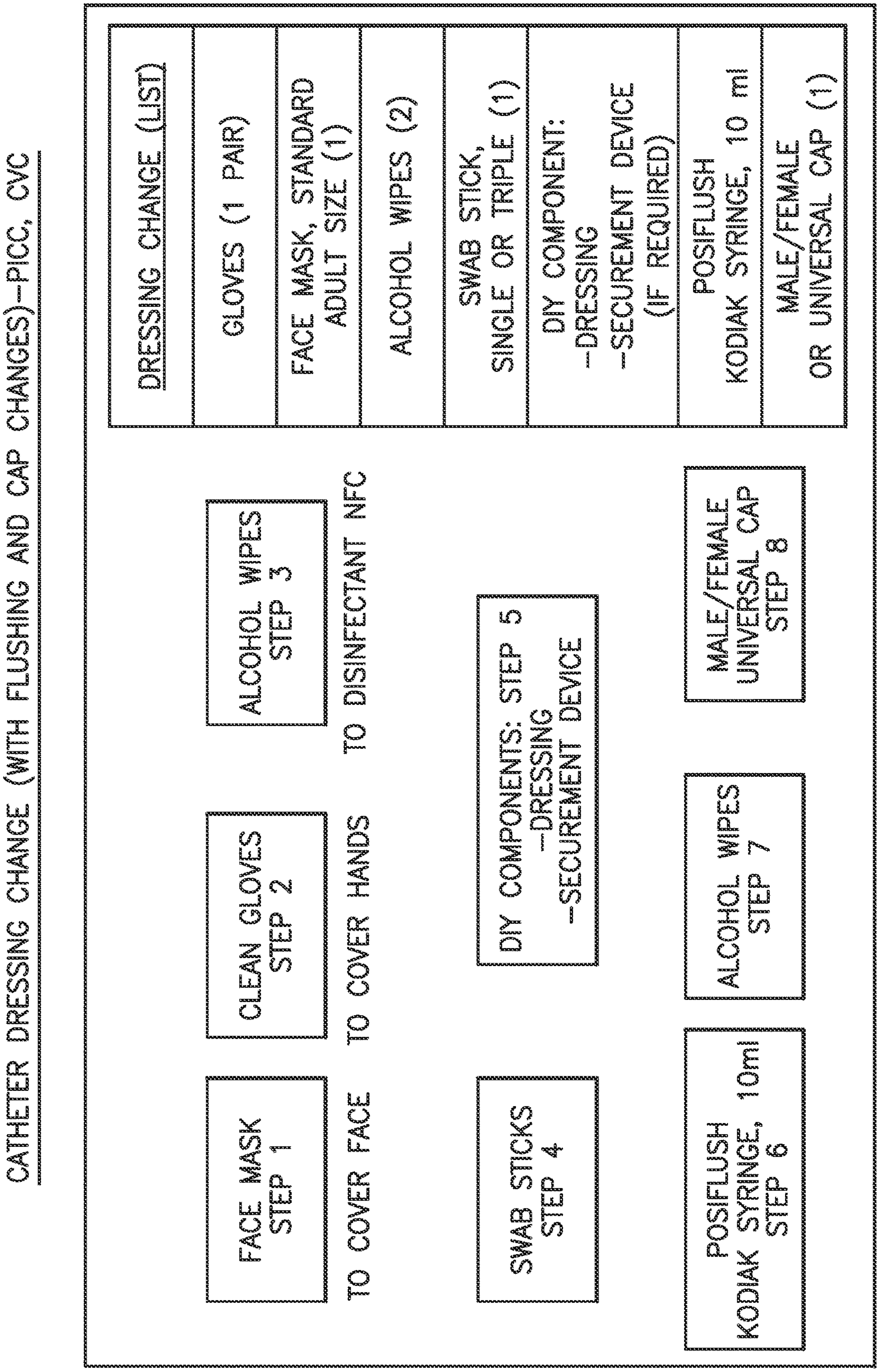
FIG. 10 is a graphical representation of medical devices and supplies included in the medical device kit of FIG. 6, according to an embodiment.
Figure 11:
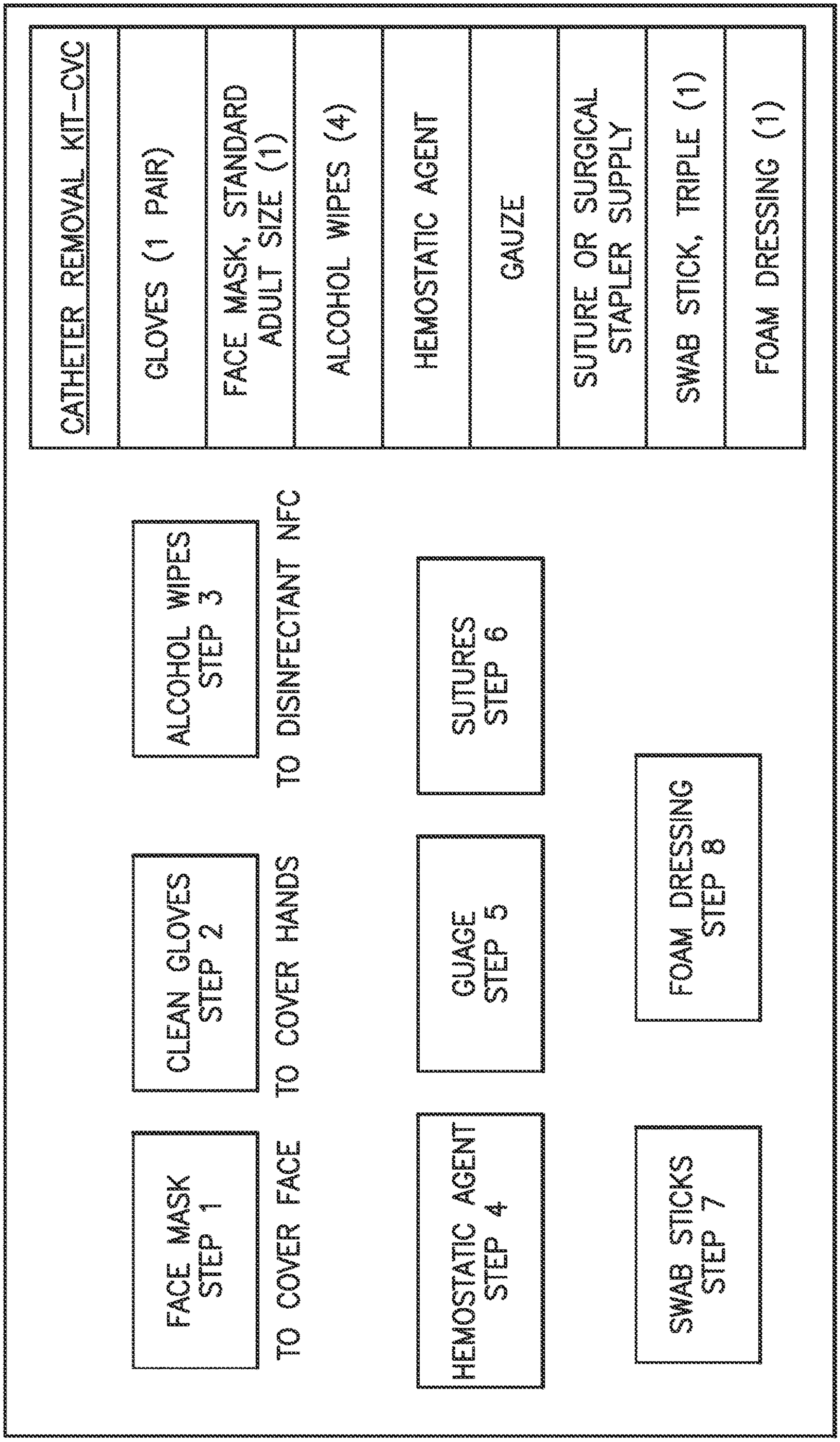
FIG. 11 is a graphical representation of medical devices and supplies included in the medical device kit of FIG. 6, according to another embodiment.
Figure 12:
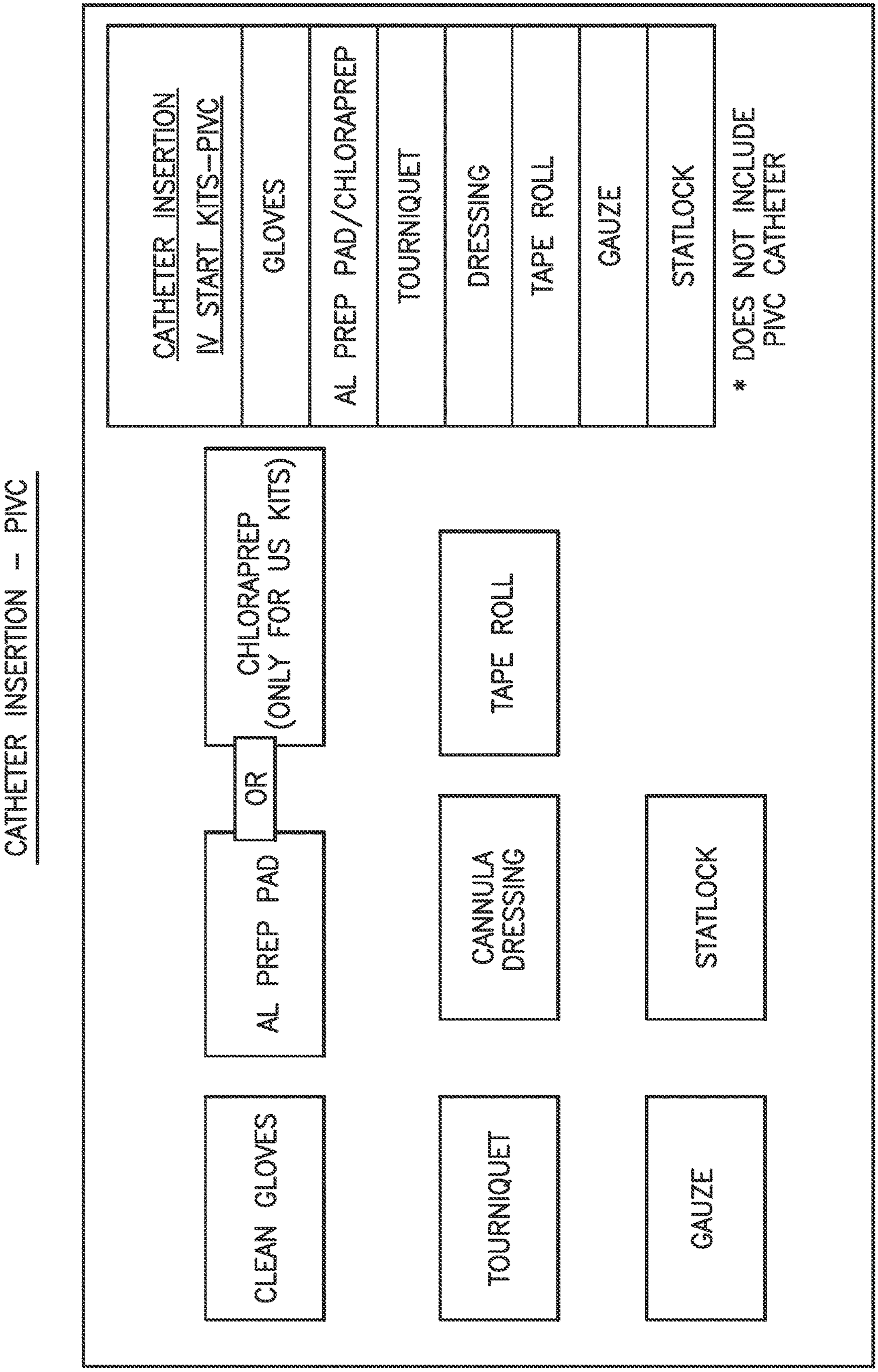
FIG. 12 is a graphical representation of medical devices and supplies included in the medical device kit of FIG. 6, according to another embodiment.
Figure 13:
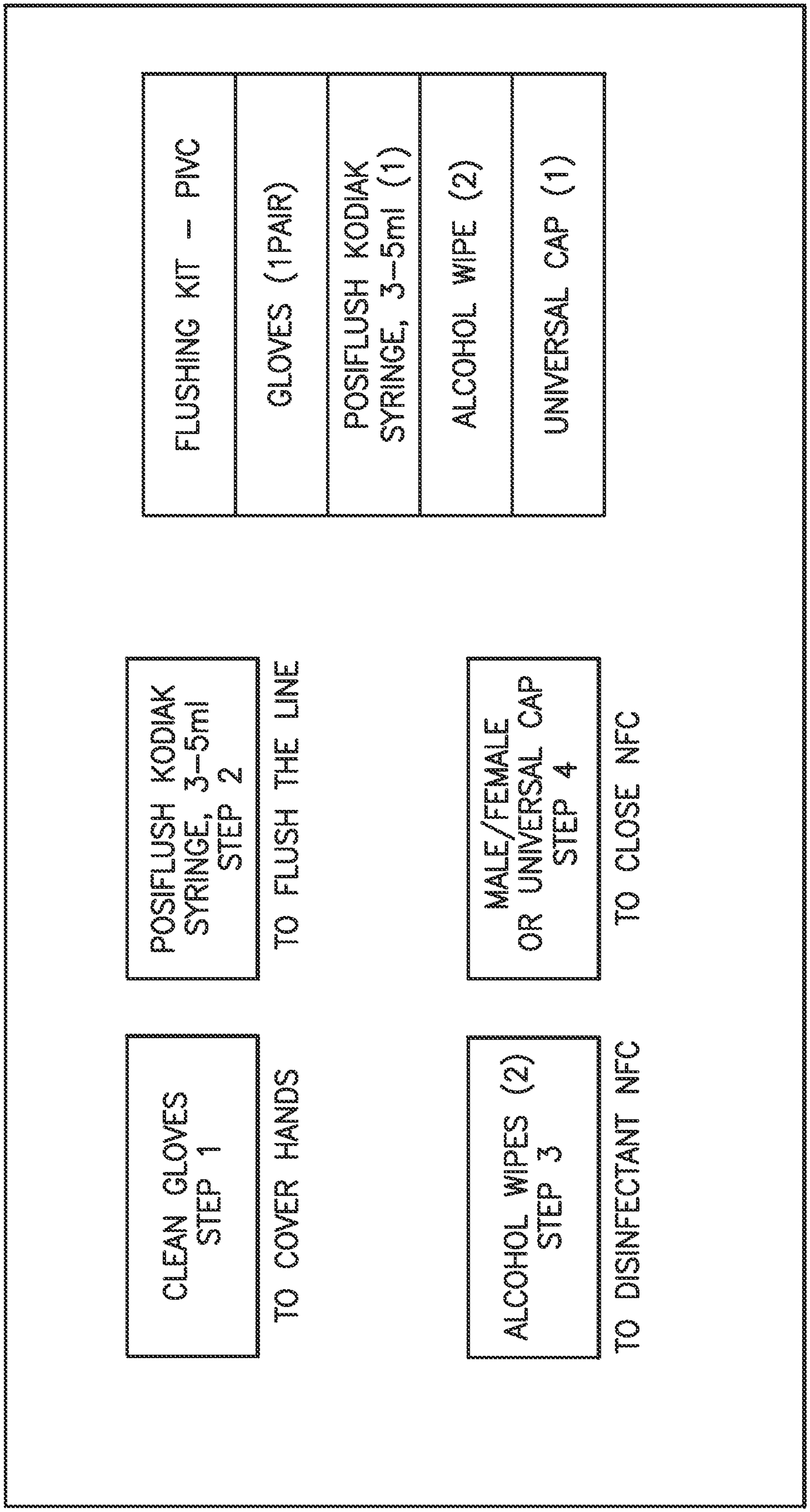
FIG. 13 is a graphical representation of medical devices and supplies included in the medical device kit of FIG. 6, according to another embodiment.

According to embodiments, and as shown in FIG. 9, each of the kit pages 108 may be configured to be torn out from the outer casing 106 as a clinician proceeds through the steps of the treatment/procedure being performed, with either an entirety of the kit page 108 being removable or just the right page region 120 being removable. A kit page 108 corresponding to a specific step (or group of steps) of the treatment/procedure may be torn out from the kit 100 (i.e., torn off of the outer casing 106) after the step(s) has been performed by the clinician, with the clinician returning used medical devices/supplies 130 (i.e., medical waste) back into the pockets 122 in which they were originally stored and then subsequently tearing the respective kit page 108 out from the kit 100 to dispose of the kit page 108 and the medical waste returned into the pockets 122 thereon. Removal of a kit page 108 after completion of the step(s) associated therewith allows the clinician to easily proceed to the next kit page 108 and helps to maintain an orderly work area via enabling the immediate disposal of the medical waste from the preceding kit page 108.

In some embodiments, the right page region 120 of each of the kit pages 108 may include one or more color coded tags 132 that provide to a clinician information on one or more of: steps of the treatment/procedure, patient information, and/or disposal information (for the medical devices/supplies after use thereof). In one example, a tag 132 included on each kit page 108 or on each pocket 122 of each kit page 108 may indicate whether the device(s) or supply(s) 130 used by the clinician for that step are a biohazard medical waste or a non-hazardous/general medical waste, so as to allow the clinician to dispose of the waste in the proper manner. As indicated above, following completion of a treatment step, the clinician may return the used medical devices/supplies 130 back into the pockets 122 in which they were originally stored and then subsequently tear the respective kit page 108 out from the kit 100 to dispose of the kit page 108 and the associated medical waste, with the color coded tag(s) 132 aiding the clinician in disposal thereof into an appropriate biohazard waste receptacle or a non-hazardous/general waste receptacle.

Following now is a work flow describing a plurality of steps to be followed by a clinician when using the kit 100 to perform a desired medical treatment or procedure. As previously described, exemplary treatments/procedures for which the kit 100 may be used include changing a catheter dressing assembly flushing an indwelling catheter, removing an indwelling catheter, or inserting a new indwelling catheter, as non-limiting examples. Examples of the medical devices and supplies 130 to be included for such procedures are shown in FIGS. 10-13, according to embodiments, with devices/supplies included for a dressing change kit (FIG. 10), a catheter removal kit (FIG. 11), a catheter insertion kit (FIG. 12), and a catheter flushing kit (FIG. 13) being set forth.

In an initial step, a clinician may receive the kit 100 in its storage configuration 102 and proceed to release or remove a fastening device 114 thereon to unlock the kit 100 and allow it to transform from a closed storage configuration 102 to an open usage configuration 104. In one embodiment, releasing the fastening device 114 includes removing an adhesive member (e.g., piece of tape) that secures the left casing region 106*a* to the right casing region 106*c*, thereby allowing the left casing region 106*a* to be opened (i.e., rotated away) from the right casing region 106*c*.

Upon the kit 100 being moved into its usage configuration 104, the clinician has access to a first kit page 108 that includes materials necessary for performing a step of the treatment/procedure being performed. The materials on the first kit page 108 include usage instructions 124 on the left page region 118 thereof and one or more medical devices or supplies 130 secured within pockets 122 on the right page region 120 thereof. The clinician may remove the desired devices/supplies 130 and use them in an appropriate order and manner according to the instructions provided for the current treatment step.

Once the clinician has finished using a particular medical device or supply as part of the first treatment step being performed, the clinician may return the used device/product 130 (i.e., medical waste) into it respective pocket 122 on right page region 120 from which it was originally removed. The clinician may then tear the first kit page 108 off from the outer casing 106 (with the medical waste retained within the pockets 122 of the right page region 120) and dispose of the kit more color coded tag(s) 132 provided on the first kit page 108 may aid the clinician in disposing the medical waste into an appropriate biohazard waste receptacle or non-hazardous/general waste receptacle.

Upon completion of the first step of the treatment/procedure and the removal of the associated first kit page 108 of the kit 100, the clinician has access to a second kit page 108 that includes materials necessary for performing a next step of the treatment/procedure being performed. The materials on the second kit page 108 include usage instructions 124 on the left page region 118 thereof and one or more medical devices or supplies 130 secured within pockets 122 on the right page region 120 thereof. The clinician may remove the desired devices/supplies 130 and use them in an appropriate order and manner according to the instructions provided for the second treatment step.

Once the clinician has finished using a particular medical device or product as part of the second treatment step being performed, the clinician may return the used device/product 130 (i.e., medical waste) into its respective pocket 122 on right page region 120 from which it was originally removed. The clinician may then tear the second kit page 108 off from the outer casing 106 (with the medical waste retained within the pockets 122 of the right page region 120) and dispose of the kit page 108 and the associated medical waste in an appropriate manner. Again, in one embodiment, one or more color coded tag(s) 132 provided on the second kit page 108 may aid the clinician in disposing the medical waste into an appropriate biohazard waste receptacle or non-hazardous/general waste receptacle.

Beneficially, embodiments of the medical device kits described herein address issues of device organization and waste disposal typically associated with use of a medical device kit. The kits provide for medical devices and supplies therein to be organized according to their order of use, so as to improve efficiency of the procedure being performed and minimize the potential for steps in the procedure to be skipped. Additionally, the kits assist with timely and proper disposal of the medical waste created thereby, so as improve efficiency in performing the procedure/treatment and prevent issues associated with improper disposal of medical waste, including bio-hazard medical waste.

Although the present disclosure has been described in detail for the purpose of illustration based on what is currently considered to be the most practical and preferred embodiments or aspects, it is to be understood that such detail is solely for that purpose and that the present disclosure is not limited to the disclosed embodiments or aspects, but, on the contrary, is intended to cover modifications and equivalent arrangements that are within the spirit and scope of the appended claims. For example, it is to be understood that the present disclosure contemplates that, to the extent possible, one or more features of any embodiment may be combined with one or more features of any other embodiment.

The invention claimed is:

1. A medical device kit for packaging medical supplies for use in a medical procedure, the medical device kit comprising:

a base sheet comprising an inner surface and an outer surface and a first base portion and a second base portion, the base sheet configurable between a folded state and an unfolded state, and the first base portion and the second base portion are configured to be separable from each other;

a first waste bin secured to the first base portion on the inner surface;

a second waste bin secured to the second base portion on the inner surface;

a plurality of pockets configured to retain medical supplies therein, wherein each of the plurality of pockets is attached to the first waste bin on an outward facing surface thereof, each of the plurality of pockets is attached to the second waste bin on an outward facing surface thereof, or the plurality of pockets is split between the first and second waste bins, with a first number of the plurality of pockets attached to the outward facing surface of the first waste bin and a second number of the plurality of pockets attached to the outward facing surface of the second waste bin; and a plurality of fastening devices configured to secure the first base portion to the second base portion when the base sheet is in the folded state and to selectively seal shut the first waste bin and the second waste bin, wherein the medical device kit is in a storage configuration when the base sheet is in the folded state, with one of the plurality of fastening devices securing the first base portion to the second base portion, wherein the medical device kit is in a usage configuration when the base sheet is in the unfolded state, with a sterile surface prep area being provided by a portion of the base sheet between the first waste bin and the second waste bin, and wherein at least one of the first and second waste bins is configured to store hazardous medical waste therein.

2. The medical device kit of claim 1, wherein each of the base sheet and the first and second waste bins is formed of a waterproof, nonwoven fabric.

3. The medical device kit of claim 2, wherein each of the first waste bin and the second waste bin is stitched to the base sheet along a bottom edge and side edges of the respective first waste bin or second waste bin, so as to define an opening between the base sheet and the respective one of the first waste bin and the second waste bin.

4. The medical device kit of claim 3, wherein the opening of the first waste bin faces a first end of the base sheet and the opening of the second waste bin faces a second end of the base sheet.

5. The medical device kit of claim 3, wherein the plurality of fastening devices comprise a plurality of hook-and-loop fasteners, the plurality of hook-and-loop fasteners including:

a base sheet hook-and-loop fastener positioned to secure the first base portion to the second base portion when the base sheet is in the folded state; and bin hook-and-loop fasteners positioned adjacent the openings of the first and second waste bins, to selectively seal the openings.

6. The medical device kit of claim 5, wherein the bin hook-and-loop fasteners comprise:

a first hook-and-loop fastener strip positioned on an inward facing surface of each of the first and second waste bins, adjacent the opening, such that a respective first hook-and-loop fastener strip is provided for each of the first waste bin and the second waste bin; and a second hook-and-loop fastener strip positioned on the inner surface of the base sheet, adjacent the opening of each of the first and second waste bins, such that a respective second hook-and-loop fastener strip is provided for each of the first waste bin and the second waste bin;

wherein, for each of the first waste bin and the second waste bin, the first hook-and-loop fastener strip is aligned with the second hook-and-loop fastener strip, such that the first and second hook-and-loop fastener strips are securable together to seal the opening of the respective first waste bin or second waste bin.

7. The medical device kit of claim 6, wherein for each of the first waste bin and the second waste bin, the first hook-and-loop fastener strip and the second hook-and-loop fastener strip each extend across an entire width of the opening of the respective waste bin, to completely seal the respective waste bin.

8. The medical device kit of claim 1, wherein the first base portion and the second base portion are positioned on opposing ends of the base sheet along a lengthwise direction.

9. The medical device kit of claim 8, wherein the base sheet comprises a tear line formed along a centerline of the base sheet, between the first base portion and the second base portion, the first base portion separable from the second base portion along the tear line.

10. The medical device kit of claim 9, wherein the first waste bin and the second waste bin are labeled or color coded, to differentiate one of the first and second waste bins for receiving packaging waste from the other of the first and second waste bins for receiving hazardous medical waste.

11. The medical device kit of claim 10, wherein one of the first waste bin and the second waste bin comprises a biohazard label positioned thereon.

12. The medical device kit of claim 1, wherein each of the plurality of pockets is adhered to a respective one of the first waste bin and the second waste bin, so as to be selectively removable therefrom.

13. The medical device kit of claim 1, wherein each of the first waste bin and the second waste bin is sized to extend across an entire width of the base sheet, and wherein each of the plurality of pockets has a width less than the width of the base sheet.

14. The medical device kit of claim 1, wherein the sterile surface prep area comprises a flat prep area extending lengthwise an entirety of a distance between the first waste bin and the second waste bin.

15. The medical device kit of claim 1, wherein the base sheet is configured to unfold in a lengthwise direction.

16. The medical device kit of claim 1, wherein each of the plurality of pockets is formed of polypropylene.

17. The medical device kit of claim 1, wherein the plurality of pockets comprises at least a first pocket and a second pocket, where the first pocket and the second pocket are sized differently, so as to be configured to accommodate different medical supplies therein.

18. The medical device kit of claim 1, wherein with the base sheet in the unfolded state, the first waste bin and the second waste bin are on opposing ends of the base sheet.

* * * * *